US00PP36276P2

(12) United States Plant Patent
Danziger

(10) Patent No.: US PP36,276 P2
(45) Date of Patent: Nov. 26, 2024

(54) ***CUPHEA* PLANT NAMED 'DCUPCUBSID'**

(50) Latin Name: *Cuphea hybrida*
Varietal Denomination: DCUPCUBSID

(71) Applicant: Danziger 'DAN' Flower Farm, Beit Dagan (IL)

(72) Inventor: Gavriel Danziger, Beit Dagan (IL)

(73) Assignee: Danziger "DAN" Flower Farm (IL)

( * ) Notice: Subject to any disclaimer, the term of this patent is extended or adjusted under 35 U.S.C. 154(b) by 0 days.

(21) Appl. No.: 18/389,384

(22) Filed: Nov. 14, 2023

(51) Int. Cl.
*A01H 5/02* (2018.01)
*A01H 6/00* (2018.01)

(52) U.S. Cl.
USPC ..... Plt./420
CPC ..... *A01H 6/00* (2018.05)

(58) Field of Classification Search
USPC ..... Plt./420
CPC ..... A01H 5/02
See application file for complete search history.

(56) References Cited

PUBLICATIONS https://issuu.com/ehrpublications/docs/ehr_101_-_2023_report; Jun. 29, 2023; 1 page.*
https://rockymountainliners.com/wp-content/uploads/2023/06/2024-RML_Catalog.pdf; Jun. 2023; 17 pages.*
https://www.bfgsupply.com/media/7520/2023-pc-spring-trials_web.pdf; 2023; 4 pages.*
https://www.carlinsales.com/media/1545/danzigerprogram-2024.pdf; 2024; 5 pages.*
https://www.danzigeronline.com/catalog/annuals/presidente/; Apr. 4, 2024; 1 page.*

* cited by examiner

*Primary Examiner* — Kent L Bell
(74) *Attorney, Agent, or Firm* — Cassandra Bright

(57) ABSTRACT

A new and distinct *Cuphea* plant named 'DCUPCUBSID' is disclosed, characterized by being sterile with a moderately vigorous habit, and a long flowering period. The plant has dark-green foliage with red-orange and cream-green colored flowers. The new variety is a *Cuphea*, normally produced as an outdoor garden or container plant.

2 Drawing Sheets

Figure 1:
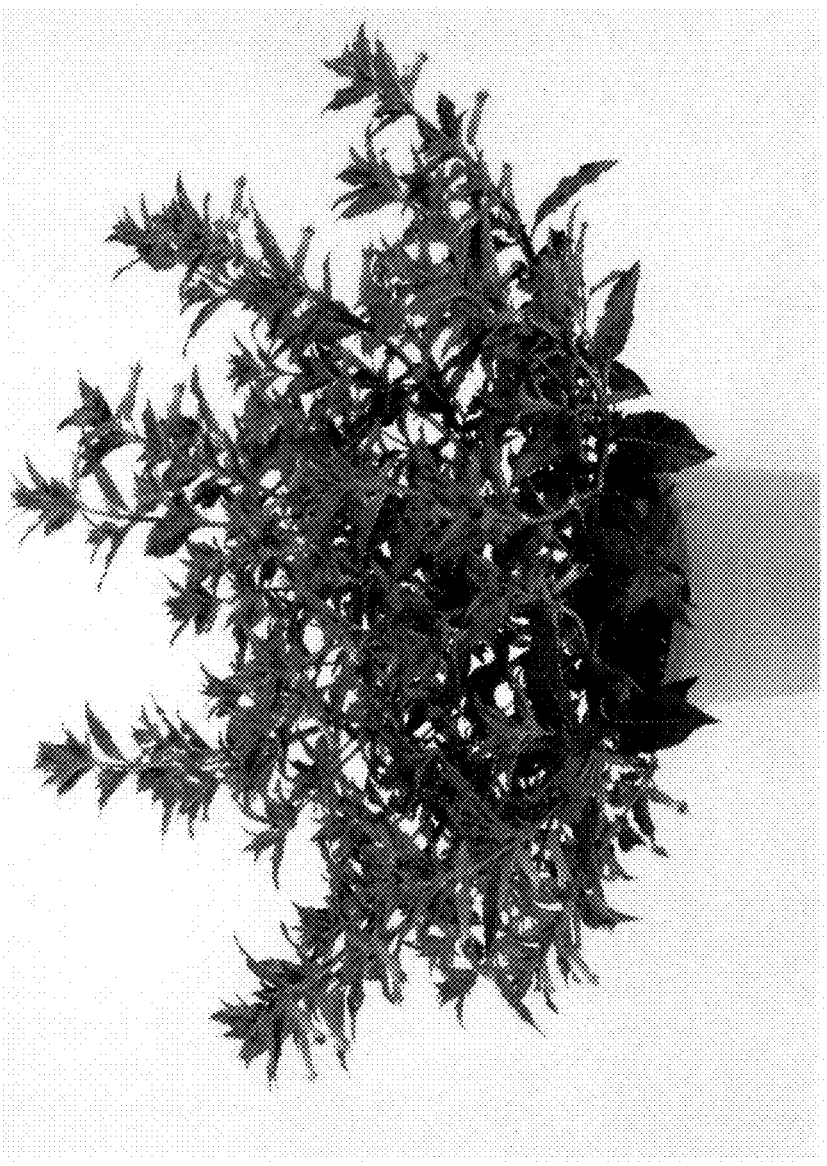

Latin name of the genus and species: *Cuphea hybrida.*
Variety denomination: 'DCUPCUBSID'.

BACKGROUND OF THE INVENTION

The new *Cuphea* plant is a product of a planned breeding program conducted by the inventor, Gavriel Danziger in Moshav Mishmar Hashiva, Israel. The objective of the breeding program was to produce new *Cuphea* varieties. The cross resulting in this new variety was made during the summer of 2018.

The seed parent is the unpatented, propriety variety referred to as *Cuphea micropetala* 'CPB-17-7010'. The pollen parent is the unpatented, propriety variety referred to as *Cuphea ignea* 'CPB-15-3101'. The new variety was discovered in May of 2019 by the inventor in a group of seedlings resulting from the parental crossing, in a greenhouse in Moshav Mishmar Hashiva, Israel.

Asexual reproduction of the new cultivar 'DCUPCUBSID' was first performed by terminal vegetative cuttings during May of 2019, at a greenhouse in Moshav Mishmar Hashiva, Israel. Subsequent propagation by terminal vegetative cuttings has shown that the unique features of this cultivar are stable and reproduced true to type in successive generations. First public access to plants of the variety occurred Dec. 25, 2022 in Italy. This offer came directly or indirectly from the inventor, qualifying for the exception allowed under 102(b). Previous to this sale, although the variety may have been publicized in print, plants were not available to the public for propagation.

SUMMARY OF THE INVENTION

The cultivar 'DCUPCUBSID' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'DCUPCUBSID' These characteristics in combination distinguish 'DCUPCUBSID' as a new and distinct *Cuphea* cultivar:

1. Sterile plants.
2. Dark green foliage.
3. Red-orange and cream-green flower color.
4. Moderately vigorous habit.
5. Long flowering period.

PARENT COMPARISONS

Plants of the new cultivar 'DCUPCUBSID' are similar to plants of the seed parent in most horticultural characteristics, however, plants of the new cultivar 'DCUPCUBSID' differ in the following;

1. Plants of the new variety are sterile, while plants of the seed parent are fertile.
2. Plants of the new variety produce more flowers than plants of the seed parent.

3. Plants of the new cultivar have a different floral tube color and size.
4. Foliage of the new variety is smaller than foliage of the seed parent.
5. Plants of the new variety produce more branches than plants of the seed parent.

Plants of the new cultivar 'DCUPCUBSID' are similar to plants of the pollen parent in most horticultural characteristics however, plants of the new cultivar 'DCUPCUBSID' differ in the following;

1. Plants of the new variety are sterile, while plants of the pollen parent are fertile.
2. Plants of the new variety have a different floral tube color and size.
3. Plants of the new variety have more vigorous, upright habits than plants of the pollen parent.

COMMERCIAL COMPARISON

Plants of the new cultivar 'DCUPCUBSID' can be compared to the commercial variety *Cuphea* 'David Varity', unpatented. These varieties are similar in most horticultural characteristics; however, 'DCUPCUBSID' differs in the following:

1. Plants of the new variety are shorter than plants of this comparator.
2. Plants of the new variety produce more flowers than plants of this comparator.
3. Foliage of the new variety is less sensitive to cold than foliage of this comparator.

BRIEF DESCRIPTION OF THE PHOTOGRAPHS

The accompanying photograph in FIG. 1 illustrates in full color a typical plant in a 20 cm pot, at approximately 5 months of age, of 'DCUPCUBSID' grown in a greenhouse, in Moshav Mishmar Hashiva, Israel.

Figure 2:
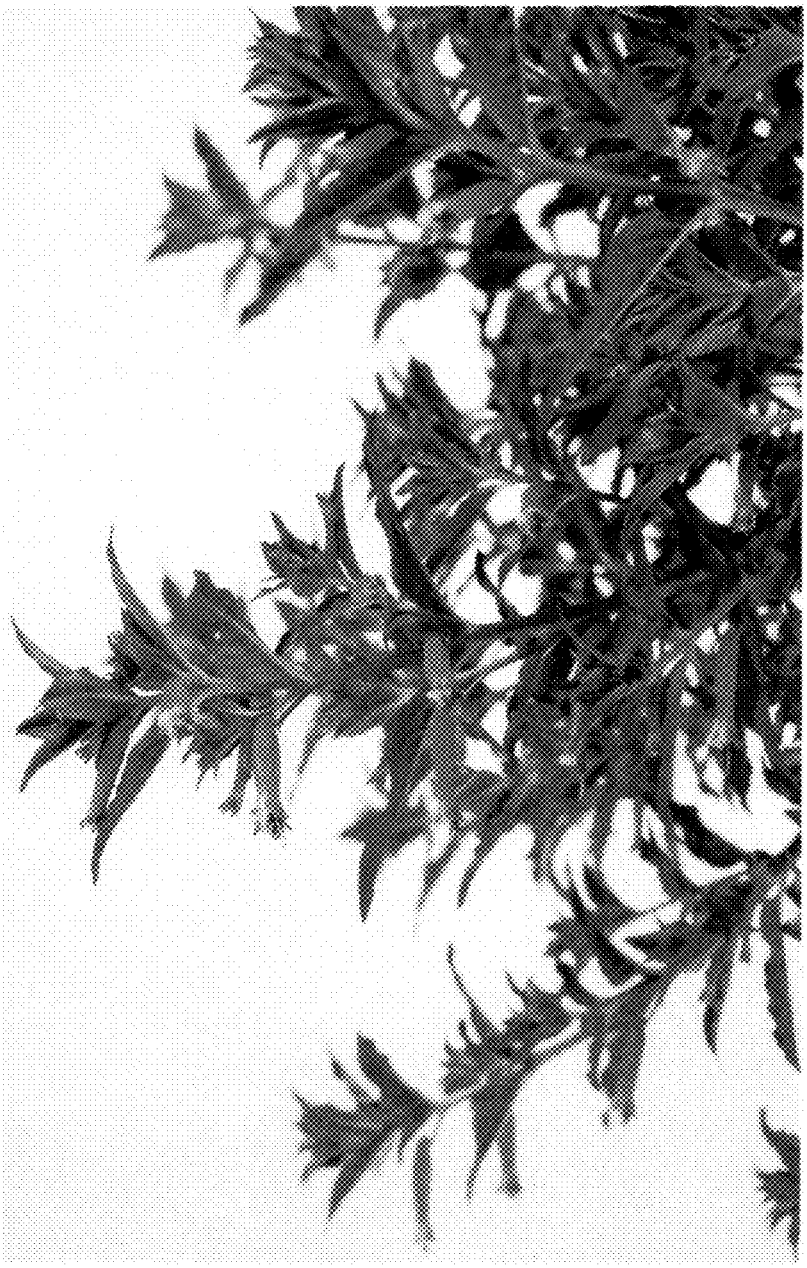

FIG. 2 illustrates in full color typical flowers and foliage of 'DCUPCUBSID'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Mini Colour Chart 2005 except where general terms of ordinary dictionary significance are used. The following observations and measurements describe 'DCUPCUBSID' plants grown in a greenhouse in Moshav Mishmar Hashiva, Israel, under natural lighting. Measurements were taken during spring of 2023. The plants were approximately 15 weeks from a rooted cutting. The growing temperature ranged from 15° C. to 28° C. during the days, 15° C. to 20° C. during the nights. Measurements and numerical values represent averages of typical plant types.

Botanical classification: *Cuphea hybrida* 'DCUPCUBSID'.

PROPAGATION

Time to initiate roots: 7 to 10 days at approximately 18° to 25° C.

Time to produce a rooted cutting: About 16 to 20 days at 18° to 30° C.

Root description: Semi-fleshy cream colored roots.

PLANT

Growth habit: Semi-upright.

Height: Approximately 50 cm (mature plant).

Plant spread: Approximately 25 cm.

Growth rate: Moderately vigorous.

Length of primary lateral branches: 45 cm.

Diameter of lateral branches: 0.6 cm.

Quantity of primary lateral branches: 3 to 4.

Characteristics of primary lateral branches:

*Color*.—RHS Yellow-Green 145C.

*Texture*.—Smooth.

*Strength*.—Strong and flexible.

Internode length: Toward the tip: approximately 1 cm; toward the base: 4 cm.

FOLIAGE

Leaf:

*Arrangement*.—Opposite.

*Quantity*.—Approximately 30 per main branch.

*Average length*.—5 cm.

*Average width*.—1.5 to 2 cm.

*Shape of blade*.—Lanceolate.

*Apex*.—Acute.

*Base*.—Attenuate.

*Margin*.—Entire.

*Texture of top surface*.—Glabrous.

*Texture of bottom surface*.—Glabrous.

*Color*.—Young foliage upper side: Near RHS Green 137B. Young foliage under side: Near RHS Yellow-Green 147B. Mature foliage upper side: Near RHS Yellow-Green 147A. Mature foliage under side: Near RHS Yellow-Green 147B.

*Venation*.—Type: Pinnate. Venation color upper side: Near RHS Yellow-Green 145C. Venation color under side: Near RHS Yellow-Green 145D.

*Petiole*.—Length: Approximately 0.3 cm. Diameter: Approximately 0.1 cm. Color: RHS Yellow-Green 145C.

FLOWER

Natural flowering season: Early spring through autumn.

Inflorescence and flower type and habit: Freely flowering. Raceme of axillary and terminal flowers. Modified calyx whose six sepals are completely fused into a floral tube.

Flower longevity on plant: 5 to 6 days.

Quantity of flowers per plant: About 300 to 350 flowers and buds per plant (mature plant). About 20 to 30 inflorescences per plant, each with 8 to 12 open flowers and 4 to 8 buds.

Inflorescence:

*Length*.—Average range 30 to 40 cm.

*Width*.—6 cm.

*Aspect*.—Upright. Outermost inflorescences outwardly curved.

Persistence: Self-cleaning.

Fragrance: None.

Bud:

*Shape*.—Oblong.

*Length*.—1 to 1.3 cm.

*Diameter*.—2 to 3 mm.

*Color*.—Near RHS Red-Orange 32A near the base; upper half near Yellow-Green 144C; tip Yellow-Green 144A.

Individual flowers: 6 sepals fused into a floral tube with a basal hypanthium and a slightly flared open apex.

*Apex of sepals*.—Cuspidate.

*Diameter*.—Approximately 0.4 cm.

*Length*.—Approximately 2.5 cm.

Petals: No petal lobes, corolla is a tube.

Floral tube:

*Color*.—When opening: Inner surface: Near RHS White NN155B. Outer surface: Near RHS Red-Orange 32A. Fully opened: Inner surface: Near RHS White NN155B. Outer surface: Near RHS Red-Orange 32A; tip White NN155B, flecked with Yellow-Green 146B. Fading: Inner surface: Near RHS White NN155B. Outer surface: Near RHS Red-Orange 32B; tip White NN155B, flecked with Yellow-Green 146C.

*Texture*.—Interior: Pubescent and slightly sticky. Exterior: Glabrous.

Peduncle:

*Length*.—Approximately 5 to 7 cm.

*Diameter*.—Approximately 5 mm.

*Color*.—RHS Yellow-Green 145C flushed Greyed-Red 179A and 179B.

*Texture*.—Glabrous.

REPRODUCTIVE ORGANS

Stamens:

*Number*.—11, dorsifixed, adnate to floral tube.

*Filament length*.—5 are approximately 0.6 cm. 6 are approximately 0.4 cm.

Anthers:

*Length*.—Approximately 1 mm.

*Shape*.—Oblong.

*Color*.—Near RHS Purple 59B.

*Pollen*.—Color: Near RHS White N155A. Quantity: Minimal.

Pistil:

*Number*.—1.

*Length*.—Approximately 1.9 cm.

*Style*.—Length: Approximately 1.9 cm. Color: Near RHS White NN155B.

*Stigma*.—Shape: Capitate, less than 1 mm. Color: Near RHS Purple-Pink N66D. Ovary Color: Near RHS White 155C.

OTHER CHARACTERISTICS

Seeds and fruits: Not observed to date.

Disease/pest resistance: Typical to known *Cuphea* varieties. Neither resistance nor susceptibility to the normal diseases and pests of *Cuphea* have been observed.

Temperature tolerance: USDA Zones 8-11.

Drought tolerance: No tolerance for drought.

What is claimed is:

1. A new and distinct cultivar of *Cuphea* plant named 'DCUPCUBSID' as herein illustrated and described.

* * * * *